US008764655B2

(12) United States Patent
Yoo

(10) Patent No.: US 8,764,655 B2
(45) Date of Patent: Jul. 1, 2014

(54) REMOTE MEDICAL DIAGNOSIS DEVICE INCLUDING BIO-MOUSE AND BIO-KEYBOARD, AND METHOD USING THE SAME

(75) Inventor: Jae Chern Yoo, Gwacheon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 677 days.

(21) Appl. No.: 12/920,873

(22) PCT Filed: Mar. 2, 2009

(86) PCT No.: PCT/KR2009/000986
§ 371 (c)(1),
(2), (4) Date: Sep. 3, 2010

(87) PCT Pub. No.: WO2009/110702
PCT Pub. Date: Sep. 11, 2009

(65) Prior Publication Data
US 2011/0015504 A1 Jan. 20, 2011

(30) Foreign Application Priority Data

Mar. 4, 2008 (KR) ........................ 10-2008-0020757

(51) Int. Cl.
*A61B 5/00* (2006.01)
*G06F 19/00* (2011.01)
*G01N 21/00* (2006.01)
(52) U.S. Cl.
CPC ................ *G06F 19/36* (2013.01); *G01N 21/00* (2013.01)
USPC ........................................................ 600/301

(58) Field of Classification Search
USPC ...................... 600/300–301; 345/163; 356/72
See application file for complete search history.

(56) References Cited

U.S. PATENT DOCUMENTS

| 5,741,217 | A * | 4/1998 | Gero ............................ 600/547 |
| 5,990,866 | A * | 11/1999 | Yollin ........................... 345/157 |
| 6,190,314 | B1 * | 2/2001 | Ark et al. ..................... 600/300 |
| 6,616,613 | B1 * | 9/2003 | Goodman ...................... 600/504 |
| 7,061,594 | B2 * | 6/2006 | Worthington et al. .......... 356/72 |
| 8,239,774 | B2 * | 8/2012 | Gandhi et al. ................ 715/752 |
| 2001/0041845 | A1 | 11/2001 | Kim |
| 2002/0118355 | A1 * | 8/2002 | Worthington et al. .......... 356/72 |
| 2003/0054376 | A1 * | 3/2003 | Mullis et al. ...................... 435/6 |
| 2005/0043583 | A1 | 2/2005 | Killmann et al. |
| 2005/0076304 | A1 * | 4/2005 | Shing ............................ 715/716 |

(Continued)

FOREIGN PATENT DOCUMENTS

| CN | 1278630 A | 1/2001 |
| CN | 1687887 A | 10/2005 |

(Continued)

OTHER PUBLICATIONS

Chinese Office Action dated Dec. 31, 2011 issued in corresponding Chinese Patent Application No. 200980107636.3.

(Continued)

*Primary Examiner* — Bill Thomson
*Assistant Examiner* — Bobby Soriano
(74) *Attorney, Agent, or Firm* — Staas & Halsey LLP

(57) ABSTRACT

Disclosed herein are a remote medical diagnostic device that includes both a bio-mouse and a bio-keyboard, and a method using the same.

29 Claims, 9 Drawing Sheets

(56) References Cited

U.S. PATENT DOCUMENTS

| | | |
|---|---|---|
| 2006/0135857 A1 | 6/2006 | Ho et al. |
| 2006/0209028 A1* | 9/2006 | Ozolins .................. 345/168 |
| 2007/0070040 A1 | 3/2007 | Chen et al. |
| 2007/0132733 A1* | 6/2007 | Ram ....................... 345/163 |
| 2008/0134101 A1* | 6/2008 | Newman ................. 715/856 |
| 2010/0056880 A1* | 3/2010 | Cho et al. ............... 600/301 |

FOREIGN PATENT DOCUMENTS

| | | |
|---|---|---|
| DE | 20104939.1 | 7/2001 |
| WO | 96/01585 | 1/1996 |
| WO | 01/75766 A1 | 10/2001 |
| WO | 2006/118420 A1 | 11/2006 |
| WO | 2007/001160 A1 | 1/2007 |

OTHER PUBLICATIONS

Extended European Search Report mailed Feb. 15, 2013 for corresponding European Application No. 09716815.7.

* cited by examiner

FIG. 2
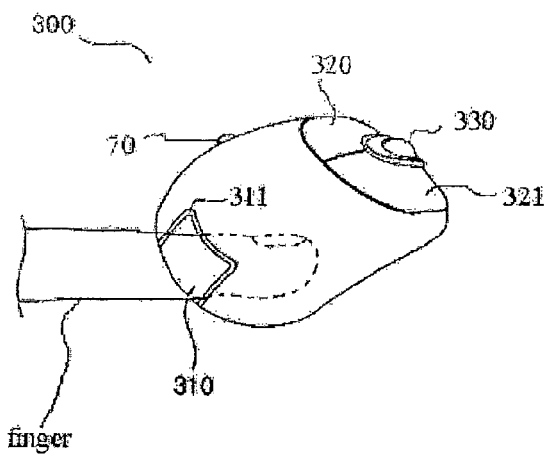
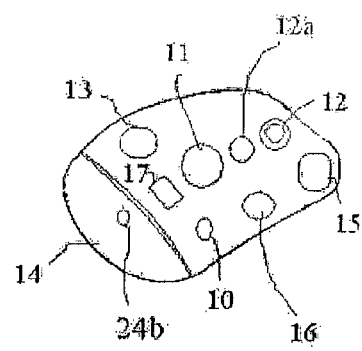
<Top View>    <Bottom View>
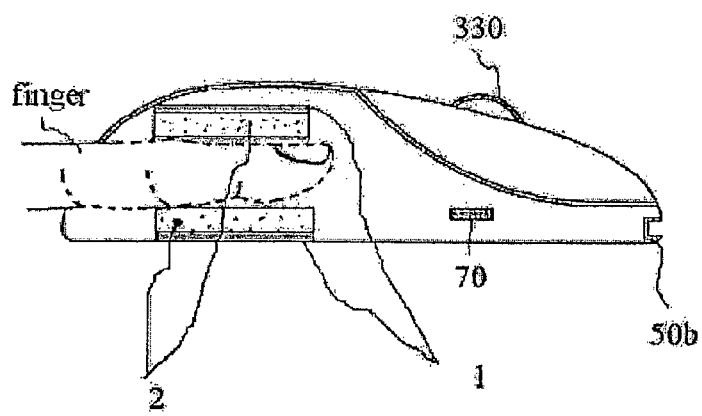
<Side View>

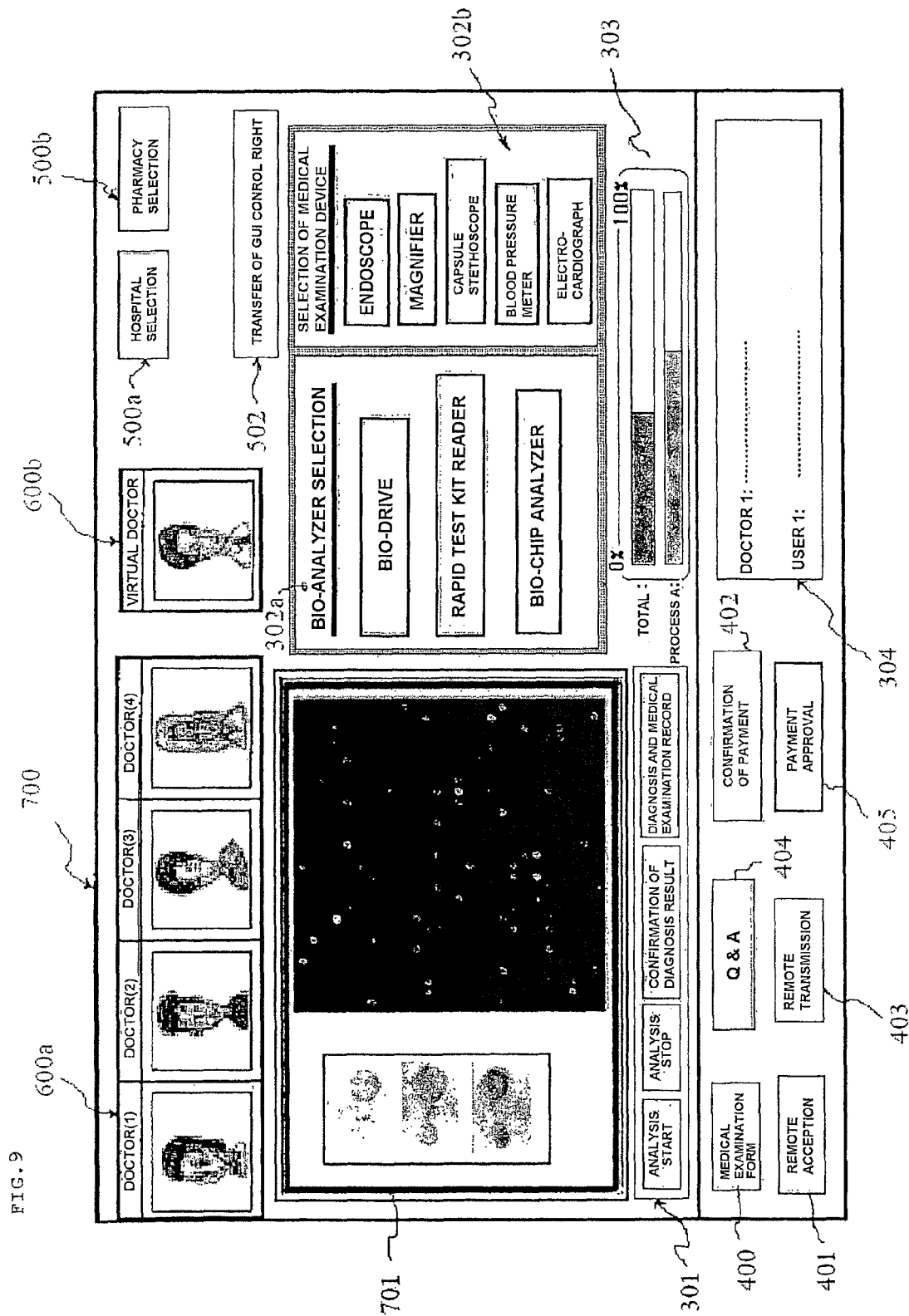

REMOTE MEDICAL DIAGNOSIS DEVICE INCLUDING BIO-MOUSE AND BIO-KEYBOARD, AND METHOD USING THE SAME

CROSS REFERENCE TO RELATED APPLICATIONS

This application claims the benefit under 35 U.S.C. Section 371, of PCT International Application No. PCT/KR2009/000986, filed Mar. 2, 2009, which claimed priority to Korean Application No. 10-2008-0020757, filed Mar. 4, 2008, the disclosures of which are hereby incorporated by reference.

TECHNICAL FIELD

Embodiments of the present invention relate to a remote medical diagnostic device including a bio-mouse and a bio-keyboard, as well as uses thereof.

BACKGROUND ART

Remote medical diagnosis techniques to provide disease diagnosis services using a telecommunication network such as the internet by a physically distant medical doctor (hereinafter, referred to as "remote doctor") are well known in related art and, for instance, such remote medical diagnosis techniques generally convert various information such as blood pressure, pulse, image information, etc. of a patient into digital signals and transmit the digital signals to a remote doctor, so as to provide a remote medical diagnosis service.

More particularly, conventionally known remote diagnosis technologies may include, for example: a remote medical diagnostic method that measures blood pressure and/or pulse of a patient, stores results thereof in a storage device, and monitors the results at a remote location through a telecommunication system; a remote medical diagnostic method that monitors image information obtained from computerized axial tomography (CAT) and/or magnetic resonance imaging (MRI) test of a patient and diagnoses the patient based on the monitored results by a remote doctor; a remote medical diagnostic method that includes frequency modulation (FM) of X-ray image and transportation thereof to a distant location (such as a remote server); a medical diagnostic method that checks the health condition of a patient daily using a home healthcare system and provides checked results to a storage device at a long distance or a remote doctor through a telecommunication network; a remote medical diagnostic method that measures body temperature, blood pressure, pulse, etc. of a patient, and stores or transports the measured results to a remote server; a remote medical diagnostic method that includes transmission of bio-signals of a patient to a remote doctor; a remote medical diagnostic method that a patient in home directly uses an electronic stethoscope so as to enable a remote doctor to perform auscultation of the patient; and a remote medical diagnostic method that uses a health care and measurement device to input ID of a patient and determine health condition of the patient, checks measured blood pressure, pulse, body weight, electrocardiogram (ECG), etc., transmits the determined data to the foregoing health care and measurement device via a telecommunication network, and receives diagnosis and final results thereof.

In general, a remote medical diagnostic method has been accomplished by providing message, audio or video-based medical consultant service of a medical doctor to a patient through a telecommunication network such as the internet or remotely instructing procedures for use of a medical examination device to a patient and, in this case, a medical doctor conducts measurement and analysis of data in the medical examination device in real-time and remotely diagnoses or, after remotely storing medical data measured by the medical examination device in a hospital server, checks and/or analyzes the stored data, and notifies the patient of diagnosis results.

However, the foregoing remote medical diagnostic methods need complicated connection of individual medical apparatuses via input/output terminals of computers in order to conduct multiple diagnoses, which are in turn tangled with existing mouse and keyboard to form a very complex user interface that is too difficult to be used by a patient. Therefore, in order to commercially and effectively use such remote medical diagnosis techniques, a novel medical examination apparatus providing a simple user interface capable of being easily used by a patient at home is strongly required. Briefly, the foregoing conventional remote medical diagnostic method was performed by separately connecting a plurality of medical devices such as a stethoscope, a thermometer, an imaging sensor, a ultrasound tester, a blood analyzer, etc. to input/output terminals of a user computer in order to use the same. Also, after using the medical devices, these should be removed from the input/output terminals and separately kept in alternative places, thus being troublesome in use. Otherwise, if the medical devices are left without maintenance, these are tangled with existing mouse and/or keyboard, thus causing a messy environment around the computer and causing a user inconvenience. As a result, remote medical diagnosis environments may be more complicated and difficult to use. Accordingly, there is still a requirement for development of more improved remote medical diagnostic devices to provide an effective user interface enabling convenient and simple use of multiple medical examination apparatuses by a user.

DISCLOSURE

Technical Problem

Therefore, embodiments of the present invention are directed to provision of a remote medical diagnostic device including a bio-mouse and a bio-keyboard, which is effective for remote medical diagnosis, as well as a method using the same.

Technical Solution

In accordance with the description of the present application, a bio-disc refers to a bio-disc, a digital bio-disc, a thin-film type chemical analytical device and/or a bio-memory disc, which are integrated with a lab-on-a chip system and applicable to, for example, various diagnostic analyzers, a nucleic acid hybrid analyzer, a biomaterial analyzer, a body constitution analyzer for personalized medicine, a urine analyzer, a blood analyzer, an environmental pollution (for example, air pollution or water contamination) analyzer, a bio-chemical analyzer, an immunological analyzer, and so forth.

In accordance with the description of the present application, a bio-disc drive refers to an instrument wherein the foregoing bio-disc may be loaded, inserted, mounted, removed and/or integrated therein, in order to drive and control the bio-disc, and measure and read reaction results thereof.

Additionally, a bio-chip may include, although not restricted to, a DNA chip, Lab-on-a chip, a protein chip, a rapid test kit, a test strip, and the like.

In accordance with the description of the present application, a bio-chip analysis device refers to an instrument wherein the foregoing-bio chip may be loaded, inserted, mounted, removed and/or integrated therein, in order to drive and control the bio-chip, and measure and read reaction results thereof.

The term 'bio-analyzer' used herein may include the bio-disc drive and/or the bio-chip analytic device described above.

In accordance with one embodiment of the present invention, there is provided a remote medical diagnostic device, including: a user computer connected to a wired or wireless Internet to send and/or receive information regarding medical services; a bio-mouse connected to the user computer via a wired or wireless network, which includes at least one medical examination device selected from a group consisting of a temperature sensor, an image sensor, a ultrasound sensor, a stethoscope sensor, a blood pressure sensor and a wireless transmission/reception sensor to send/receive information of capsule endoscope, as well as an optical mouse part; a bio-keyboard including a computer keyboard, a tray on which a bio-disc or optical disc may be horizontally loaded, a motor for rotating the loaded bio-disc or optical disc, and a bio-disc drive; and a central processing unit (CPU) mounted on the user computer to provide a graphical user interface (GUI) to the user.

More particularly, the remote medical diagnostic device according to the embodiment of the present invention has a user computer connected to a wired or wireless Internet to send/receive medical service information. The user computer may be connected to a wired or wireless Internet, thus requesting medical consultant services or sending/receiving medically determined results.

The remote medical diagnostic device according to the embodiment of the present invention may also include a bio-mouse connected to the user computer via a wire or wireless network, which includes at least one medical examination device selected from a group consisting of a temperature sensor, an image sensor, a ultrasound sensor, a stethoscope sensor, a blood pressure sensor and a wireless transmission/reception sensor to send/receive information of a capsule endoscope, as well as an optical mouse part.

The computer mouse is an input tool to provide a coordinate value on a computer screen and select a specific object or execute the same, and is generally used together with a keyboard. Such a computer mouse is used as an effective computer peripheral device since a computer operating system and applied programs are changed into a GUI mode. The computer mouse is generally classified into a mechanical mouse using a ball and an optical mouse using an optical sensor. Development of a computer mouse which may be used not only as a simple tool for inputting information but also as a hybrid device to perform multiple tasks, is being currently conducted. For instance, the computer mouse may have a wired telephone module built therein to drive a modem, thus performing telephone call or data communication.

The foregoing bio-mouse of the remote medical diagnostic device according to the embodiment of the present invention has at least one medical examination device and an optical mouse part, wherein the bio-mouse is used as a computer mouse at ordinary times, while functioning as a medical examination device when a mouse mode selecting switch is changed from a general mode to a medical examination mode. The bio-mouse having multiple medical examination devices integrated therein does not need to combine the mouse with these devices, respectively, or individual medical examination devices do not need to be removed from input/output terminals and kept in alternative places after using the same. Briefly, if only the existing computer mouse is replaced by the foregoing bio-mouse without upgrading the computer for remote medical diagnosis, different remote medical diagnoses including blood test, stethoscope examination, ultrasound scanning, temperature test, oral examination, blood pressure test, etc. may be conducted using the medical examination devices built in the bio-mouse. The bio-mouse may further have a selection switch to select a general mode or a medical examination mode. The bio-mouse may further include at least two light receiving lenses to switch light receiving characteristics according to either the general mode or the medical examination mode, or a mouse wheel having a multi-colored LED to display the general mode and the medical examination mode.

The bio-mouse in a medical examination mode shifts to a particular examination site of the body of a user or a standard medical examination site and examines the same, thus improving accuracy in measurement of body temperature and/or pulse. Spatial shifting of the bio-mouse may be performed by, for example, moving the bio-mouse to a standard examination position of a medical examination device, which is provided by GUI or by a virtual doctor, moving the bio-mouse to a directed cursor position at which a particular examination site of the body of a patient is presented by movement of the mouse of a remote doctor, or moving the bio-mouse to the particular examination site of the body of a patient according to indication of a remote doctor who monitors the patient through a camera capturing images in real time. The directed cursor may be provided and controlled by the remote doctor. The virtual doctor means an imaginary doctor supported by GUI of a user's computer to analyze measured values using medical examination software and notify the user of diagnosis results, and is permanently presented in the user's computer (referred to as 'user computer'). The medical examination software may include specific software containing overall know-how and knowledge of medical specialists to analyze signals metered by a medical examination device and estimate diagnosis results from the analyzed values.

The bio-mouse may further include an animal RF ID (Radio Frequency Identification) or a RF ID reader to read contents of RF IC of the bio-disc. The animal RF ID is prepared in a form of being injected into the body or attached to an outer face of the body, and contains an inherent identification number of each animal. The RF ID and the RF IC may comply with international standards ISO 11784 and 11785 or slightly modified regulations of the same. Such international standards are well known and the RF IC may comprise personal coded information and ID of a bio-disc, in order to prevent unfair use of the bio-disc by a third party or reading of information stored in the bio-disc. Also, the RF ID has a stick tag, in which some information of an animal such as a livestock animal or a wild animal, for example, species, age, origin, etc. are recorded, and can use radio frequency to wirelessly recognize desired information by the RF ID reader. The animal RF ID can enable tracing of disease history when livestock diseases such as bovine spongiform encephalopathy (BSE) so-called aka mad cow disease, foot-to-mouth disease, avian influenza (AI), etc. are developed, thereby enabling rapid and effective animal health control. Especially, if information of livestock is associated with slaughtering, meat processing and distribution steps, accurate information of meat foods may be provided to consumers.

The bio-mouse may further include a rechargeable battery. The bio-mouse may be detachable, and the battery is rechargeable while being connected to a user computer. The bio-mouse may be connected to the user computer by a USB cable or a wireless telecommunication tool. When using the USB cable to connect the bio-mouse to the user computer, the battery may be recharged. When the bio-mouse is removed from the user computer, the bio-mouse may be activated by the battery power, in order to transport data obtained from multiple medical examination devices to the user computer through the wireless telecommunication tool. Such a wireless telecommunication tool may be, for example, Bluetooth.

While the bio-mouse is removed from the user computer, measured data from the medical examination device of the bio-mouse may be transported to a remote doctor or the user computer by cable connection between the bio-mouse and a mobile phone.

In order to store data obtained from the medical examination device while the bio-mouse is removed from the user computer, the bio-mouse may further include a memory part. The stored data in the memory part may be placed in a hard disc (HDD) of the user computer when the bio-mouse is again connected to the computer or, otherwise, may be transported to a remote doctor or a remote medical diagnosis server.

The bio-mouse may also include a memory to store product information such as version, production year, production ID of the bio-mouse, etc. as well as the data obtained from the medical examination device. Meanwhile, a bio-keyboard may include a memory to store data obtained from the bio-mouse and product information such as version, production year, and production ID of the bio-keyboard.

The product ID stored in the memory is provided to the remote medical diagnosis server through GUI in order to conduct recognition of the bio-mouse and the bio-keyboard.

Temperature measurement using a temperature sensor of the bio-mouse is performed by spatially shifting the bio-mouse to at least one site of the body of the user and combining temperatures measured at several sites to mathematically operate, thus estimating the final body temperature. The temperature sensor may include a non-contact temperature sensor or an infrared sensor. Temperatures of individual parts of the body are converted into digital data by an A/D converter and transported to a digital signal processing part in order to estimate the body temperature through mathematical calculation.

An image sensor in the bio-mouse may further have an enlarging/reducing device (that is, a zooming device) and a focus controller (that is, a focusing device). Such devices for enlarging/reducing or focusing the image sensor may be controlled in real time by a remote doctor if a right for control is assigned to the remote doctor. Real time control of the zooming device and/or the focusing device in the image sensor executed by the remote doctor may enable more convenient or simple oral examination by the doctor. Oral conditions captured by the image sensor may be displayed on a monitor or remotely transported in real time. The assignment of control right means transfer of remote GUI control right to the remote doctor. Accordingly, the remote doctor having remote GUI control right may control behavior of GUI and the image sensor or monitor the same in real time. The zooming device may comprise an optical zoom to decrease or increase a focal length by performance of multi-combined lenses, thus enlarging or reducing an image size. The image sensor may further include a high brightness LED for illumination. The image sensor or GUI may also include a brightness controller for the foregoing LED. Enlarging/reducing function of the optical zoom in the image sensor may be conducted by rotation of a mouse wheel. That is, the optical zoom may be enlarged or reduced according to a direction of rotating the mouse wheel. The focus distance may be controlled by clicking either a left button or a right button of the mouse. For example, the focal length becomes increased by clicking a left button while it becomes decreased by clicking a right button.

A stethoscope sensor in the bio-mouse refers to a sensor to output audio signals such as pulse, heart sound or breath sound generated in the body of a patient, and may include: a vibration sensor to sense vibration according to sound generated in the body by contacting the sensor with a particular site of the body; a microphone to transform the vibration from the vibration sensor into an electrical sound signal; a digital signal processor to convert the electrical sound signal into digital data and regulate and output the electrical sound signal with a stethoscope frequency bandwidth (for example, wide region (20 Hz to 4 KHz), bell (20 Hz to 500 Hz), diaphragm (200 Hz to 1 KHz)); and a sound output part to output the sound from the digital signal processor. The electrical sound signal output from the digital signal processor may be stored in a memory or a hard disc, or be transmitted to the remote doctor via Internet. The vibration sensor may have at least one selected from a diaphragm, a piezoelectric ceramic and a piezoelectric plastic film. The piezoelectric plastic film may be prepared using poly vinylidene fluoride (PVDF). The foregoing stethoscope sensor may collect sounds generated in the body, convert the same into electrical sound signals, and output the converted signals via a speaker or transmit the same in real time to a remote doctor, thereby allowing the remote doctor to listen to the heart beat. A pattern of the electrical sound output from the stethoscope sensor may be displayed on a monitor screen in order to compare the same with a standard sound pattern stored in a database. The bio-mouse spatially shifts to a particular examination site of the body or a standard medical examination position and measures the sound.

An ultrasound sensor in the bio-mouse is a device to convert sound waves reflected from internal organs of the body or a human fetus into an image, and may comprise an ultrasound probe (an ultrasound transducer), a beam generator, a digital filter and an image processor. Ultrasounds may include, for example, abdominal ultrasound, cardiac ultrasound, thyroidal ultrasound, vascular ultrasound, ultrasound in obstetrics and gynecology, urological ultrasound, etc. The ultrasound probe may have an ultrasound module comprising, for example: a piezoelectric layer wherein a piezoelectric material vibrates to execute mutual-conversion of electrical signal and acoustic signal; a matching layer to decrease a difference in acoustic impedance between the piezoelectric layer and the human body, so as to maximize transfer of ultrasound generated in the piezoelectric layer to a target position; a lens layer to focus ultrasound, which progresses toward a front of the piezoelectric layer, at a specific point; and a backing layer to prevent the ultrasound from progressing toward a rear side of the piezoelectric layer, so as to prevent image distortion. The ultrasound probe may comprise a single ultrasound element or a plurality of ultrasound elements. The ultrasound probe may be classified according to different references such as the number of ultrasound elements, arrangement of ultrasound elements, shape of alignment axis of ultrasound elements, application fields thereof, and the like. For classification based on the number of ultrasound elements, the probe may be divided into a group of single element type ultrasound probes and another group of multi-element type ultrasound probes. The multi-element type ultrasound probes may also be sorted into a first-dimensional arrangement type ultrasound probe wherein ultrasound elements are arranged on a single axis and a second-dimensional arrangement type ultrasound probe wherein ultrasound elements are arranged on multiple crossing axes, according to arrangement of ultrasound elements. According to the shape of the alignment axis of ultrasound elements, the first-dimensional arrangement type ultrasound probe may further be classified into a linear array type ultrasound probe and a curvilinear array type ultrasound probe. The foregoing ultrasound probe receives an ultrasound signal reflected from a desired region and converts the ultrasound signal into an electrical signal. The beam generator serves to delay and combine echo signals received by the ultrasound probe elements. Signals of the beam generator are converted into digital data by an A/D converter, in turn passing through a digital filter to remove noise and finally an image processor in order to display final data obtained from the ultrasound sensor on a monitor screen. The digital filter and the image processor in the ultrasound sensor may be embodied by driven software of the user computer or the digital signal processor. The ultrasound scanning may be utilized, for example, in self-diagnosis of breast cancer by a virtual doctor or remote self-diagnosis of breast cancer by a remote doctor.

A blood pressure sensor in the bio-mouse may comprise a finger hole into which a finger connected to a finger cuff is inserted for blood pressure check, a door to open or close the finger hole, and the finger cuff to apply pressure to the finger in up and down directions and/or right and left directions. More particularly, the finger cuff may be a vertical finger cuff pressing the finger upward and downward or a horizontal finger cuff pressing the finger in right and left directions. The vertical and horizontal finger cuffs are suitably integrated in the bio-mouse. For instance, the finger cuff may have an inflatable bladder built therein, which is expandable by a pump and the finger cuff applies pressure to a finger when the bladder is expanded, thus locking up finger arteries. The door may be opened/closed in up and down or right and left directions.

The blood pressure sensor may comprise, for example: a photoplethysmorgraphic (PPG) signal detection part which includes a pressurizing part to feed pressurized air at a preset pressure level for the finger cuff, an air exhausting part to discharge air of the finger cuff at a high or low speed during measurement of blood pressure, a pressure signal detection part to receive pulse vibration transferred from a finger to the finger cuff and to convert the vibration into electric charge, an LED part to detect a PPG signal, and an optical sensor; and a temperature signal detection part to detect a temperature signal of a finger using a temperature sensor. The blood pressure sensor may further have: an A/D converter which receives signals from the PPG signal detection part, the temperature signal detection part and the pressure signal detection part, and converts the received signals into digital signals; and a digital signal processor to calculate a blood pressure value by operation of the PPG signal, the temperature signal and the pressure signal. The blood pressure sensor applies pressure to a finger using the finger cuff to lock up finger arteries while measuring PPG signal from the finger by release of the pressure, thus determining blood pressure. The pressure detection part may be a bellows sensor. The digital signal processor operates upon a variation in electric charge generated in the bellows sensor, the PPG signal and the temperature signal, so as to calculate a highest blood pressure and a lowest blood pressure. Behavior of the blood pressure sensor is starting by pushing a start button of the GUI for measurement of blood pressure or, otherwise, a start button of the bio-mouse for measurement of blood pressure. For example, by clicking the start button for measurement of blood pressure after inserting a finger into the finger hole, the blood pressure sensor begins measurement of blood pressure.

A measured signal obtained from the medical examination device of the bio-mouse is firstly converted into a digital signal, transferred to the bio-keyboard through a wireless or wired telecommunication network, and processed by the digital signal processor built in the bio-keyboard, in turn being converted into measured data. For instance, since the physical size of the bio-mouse makes integration of all electronic circuits therein difficult, only major electronic circuits such as sensors are built in the bio-mouse, whilst other parts such as the digital signal processor are distributed and fixed inside the bio-keyboard. Otherwise, functions of the digital signal processer are partially embodied by software permanently present in the user computer. As a result, the bio-mouse and the bio-keyboard may be considerably reduced in size.

The foregoing GUI may have a selection button for medical examination devices, and the bio-mouse may further include another selection button for medical examination devices. The bio-mouse may also have a mouse mode selection switch to select either a general mode or a medical examination mode. In particular, the bio-mouse can select the general mode or the medical examination mode by the mouse mode selection button of the GUI or the mouse mode selection switch. The bio-mouse may function as a general computer mouse in the general mode. Also, when the bio-mouse is shifted on a mouse pad during the medical examination mode, the mode may be temporally switched to the general mode. If the bio-mouse leaves the mouse pad, it is again automatically switched to the medical examination mode. Additionally, using the image sensor in the bio-mouse, it is possible to determine whether the bio-mouse is in contact with the mouse pad or leaves the same. Such tasks may be attained since the image sensor recognizes and memories a color of the mouse pad in the general mode.

The bio-mouse may have functions of an optical mouse, and include a plurality of light receiving lenses in order to select separate lenses according to the general mode or the medical examination mode. A body surface of the user shows in general different optical reflection properties from those of a typical mouse pad. Therefore, different light receiving lenses are selected in the medical examination mode and the general mode, respectively. The foregoing GUI in the medical examination mode selects a light receiving lens different from that used in the general mode, thereby observing coordinate shifting of the bio-mouse on the body surface of the human during the medical examination mode. The bio-mouse may also include a multi-colored mouse wheel to distinguishably express the general mode and the medical examination mode, thus altering the color of the mouse wheel. For instance, the mouse wheel may turn blue to indicate the general mode while turning red color to indicate the medical examination mode.

A capsule endoscopy allows observation of interior of the body of a patient through a capsule type endoscope when the patient swallows the endoscope. The capsule endoscope moves around the inner part of the body, captures images and transmits the captured images outside in a wireless mode, in turn enabling observation of the inner body of the patient by a doctor. Principles of the capsule endoscopy are substantially well known.

The bio-mouse may include a position controller to regulate a position and a posture of the capsule endoscope within the body, and an RF generation part to supply energy to the capsule endoscope. The position controller may be a permanent magnet or electromagnet. For example, the permanent magnet or electromagnet can adjust attraction or repulsion applied to the capsule endoscope, thus controlling the position and/or posture of the capsule endoscope. For instance, attraction and repulsion applied to the capsule endoscope are adjusted by spatially shifting the bio-mouse in right/left or up/down directions on a body surface near the capsule endoscope contained in the body, clicking a button of the bio-mouse or rotating a wheel of the bio-mouse, thereby enabling control of the position and/or posture of the capsule endoscope.

A power source of the capsule endoscope may be provided using a small battery or by radio-frequency (RF) induction. The bio-mouse may include an RF generation part to supply energy to the capsule endoscope inside the body through RF induction. The small battery causes increase in size and weight of the capsule endoscope and has a drawback of relatively short time for supplying power to the capsule endoscope. On the contrary, RF generated by the RF generation part can activate an induction coil in the capsule endoscope according to Fleming's rule and sufficiently produce electric charge, thus supplying power to an image sensor and a wireless transmitter/receptor of the capsule endoscope in real time.

The capsule endoscope should transmit image information of the inner part of the body to an external reception sensor. However, owing to requirement for miniaturization of the capsule endoscope, transmission power is duly reduced. Accordingly, receive sensitivity of a receiving sensor to receive image information of the inner body is very important. The bio-mouse may closely contact a wireless transmission/reception sensor with a body surface, wherein the sensor can receive or control images of the inner body transmitted from the capsule endoscope in a wireless mode, thereby improving receive sensitivity of the sensor. Briefly, by closely contacting the bio-mouse the capsule endoscope with the body surface at a position close to a site of the capsule endoscope, the receive sensitivity of the wireless transmission/reception sensor may be maximally increased. Furthermore, in order to directly influence the capsule endoscope with magnetic force of a permanent magnet or electromagnet as a position controller of the capsule endoscope, the permanent magnet or electromagnet should be positioned closely to the capsule endoscope. This requirement is satisfied by closely contacting the bio-mouse with a body surface close to the capsule endoscope in order to apply attraction and repulsion to the capsule endoscope. Alternatively, in order to efficiently send RF generated from the RF generation part to an induction coil of the capsule endoscope, the RF should approach the capsule endoscope as close as possible. This requirement is satisfied by closely contacting the bio-mouse with a body surface near to the capsule endoscope and leading RF generated from the RF generation part to an induction coil built in the capsule endoscope.

An electrocardiogram (ECG) sensor in the bio-mouse is used to measure ECG and the number of heart beats and monitor variation in body for a constant time, and allows a remote doctor to perform emergency treatment if abnormal conditions in ECG and/or the number of heart beats are observed. Electrical impulse occurs during myocardial activity, thus generating action potential. Such action potential is transferred to a body surface and recorded as a waveform by current, thus displaying ECG by the ECG sensor. Since myocardial excitation occurs in the venous sinus and progresses toward atria and ventricles, heart active current may be plotted as a graph by inducing such excitation to a current meter (electrocardiograph) at two random points. Data obtained herein refers to electrocardiogram, that is, ECG, which is very useful for diagnosis of heart diseases. ECG may be obtained by conventional methods, for example, twin lead dipole such as 'standard limb lead' wherein both hands (first lead), right hand and right leg (second lead), left hand and left leg (third lead) are used, as well as 'unipolar limb lead,' 'precordial lead,' and so forth. ECG is used in a wide range of applications, for example: diagnosis of coronary artery diseases such as angina pectoris or myocardial infarction and various abnormal conditions of accessory arteries, electrolyte disturbances, etc.; examination of heart problems during surgical operation, and so forth. Moreover, ECG is very important in diagnosis of heart diseases.

A remote medical diagnostic device according to one embodiment of the present invention may include a bio-keyboard comprising a computer keyboard, a tray on which a bio-disc or an optical disc is horizontally loaded, a motor to rotate the loaded bio-disc or optical disc in the tray, and a bio-disc drive controlling the same.

The foregoing bio-disc may include at least one device selected from a group consisting of a disease diagnostic analyzer, a nucleic acid hybrid analyzer, a biomaterial analyzer, a body constitution analyzer for personalized medicine, a urine analyzer, a blood analyzer, an environmental pollution analyzer, a bio-chemical analyzer and an immunological analyzer. For example, the bio-disc may include a bio-disc, a digital bio-disc, a thin-film type chemical analytical device and/or a bio-memory disc which are integrated with a Lab-on-a chip system and useful for any one device selected from a group consisting of a diagnostic analyzer for various diseases, a nucleic acid hybrid analyzer, a biomaterial analyzer, a body constitution analyzer for personalized medicine, a urine analyzer, a blood analyzer, an environmental pollution analyzer, a bio-chemical analyzer and an immunological analyzer.

The bio-disc may include a control valve to regulate fluid flowing necessary to form 'lab-on-a chip' and an analytic device to analyze biomaterials, for example, a bio-substance, a target substance under environmental examination, etc. Also, the bio-analyzer may comprise: a Lab-on-a chip with an applied ELISA analysis method; another Lab-on-a chip with an applied rapid testing method; a further Lab-on-a chip used for various tests including pathogen test, residual antibiotic examination, residual pesticide analysis, genetic modified food test, air pollution examination, water contamination examination, food allergy test, paternity test (gene test to confirm family ties), meat type and origin identification test, etc.; and a small or thin-film type analyzer to diagnose and detect a slight amount of biomaterials and/or chemical materials in a fluid.

The foregoing bio-analytic device may analyze various blood and urine samples as well as biomaterials in quantitative and qualitative modes, so as to conduct various examinations, for example: cancer test; glucose monitoring; blood typing; examinations of body fat, obesity, blood viscosity, blood pressure, cardiovascular disease, etc.; blood oxygen saturation monitoring; body constitutional analysis for personalized medicine; Alzheimer and dementia examination; examination of liver disease, cardiovascular disease, myocardial infarction, etc.; AIDS test; environmental pollution monitoring; venereal disease examination; pregnancy test; gene test; and examinations regarding other diseases including GOT, GPT, cholesterol, etc.

The environmental pollution monitoring may include, for example: water contamination analysis to measure heavy metal contamination or *E. coli* content; and air pollution analysis to measure heavy metal contamination such as organic mercury, CN compounds, organic phosphorous, cadmium, arsenic, phenol, copper (Cu), lead, chromium, etc., and to analyze contents of sulfur dioxide ($SO_2$), dust (TSP), carbon monoxide (CO), nitrogen dioxide ($NO_2$), hydrocarbon (HC), ozone ($O_3$), lead (Pb), etc. in air.

Analysis of a urine sample may include analyses of leucocytes, blood, protein, nitrite, pH, specific gravity, glucose, ketone, ascorbic acid, urobilinogen, bilirubin, body fat, blood pressure, etc.

The biomaterials may include, for example, DNA, oligonucleotide, RNA, PNA, ligand, receptor, antigen, antibody, milk, urine, saliva, hair, agricultural crop and vegetable samples, meat sample, fish sample, bird sample, waste water (contaminated water), livestock sample, food sample, food material, stored food, oral cell, tissue sample, sperm, protein and other biomaterials.

The bio-disc may contain, for example, a protocol for Lab-on-a chip, an analysis algorithm, standard control values for reading and position information of analyzed sites, bioinformatic information, self-diagnosis information, device drive software for bio-disc drive and patient education information for clinical trial, web sites and links for connection with professional clinics and hospitals based on diagnosis results, memory built-in RF IC (or RFID tag) embedded in the bio-disc to store personal security information, etc.

The bio-disc drive is used to insert, mount, load and unload, or integrate the bio-disc thereon in order to drive and control the same, thus measuring and reading reaction results thereof. The bio-disc may be driven and controlled by the bio-disc drive.

Therefore, the foregoing remote medical diagnostic device may determine and read reaction results of an assay site in the bio-disc using an optical measurement device, an electrochemical measurement device, a fluorometer, an impedance measurement device or a detector combined with a converter having an image sensor, wherein the read information is processed into digital information by a computer program and transmitted/received through existing telecommunication network such as Internet, in turn providing remote medical diagnosis service to a doctor and a patient.

More particularly, the remote medical diagnostic device may have a number of applications, for example: On/Off control of a bio-analyzer or a medical examination device through GUI; monitoring behavior of the bio-analyzer or the medical examination device; receiving analyzed data from the bio-analyzer or the medical examination device and displaying the same in a numerical or graphic mode; provision of remote medical diagnosis service by a virtual or real doctor; remote analysis of environmental contaminants; requesting medical consultant service through Internet after user authentication using a user identification system and obtaining medical consultation of a medical specialist; provision of desired medical diagnosis services; transmission of medical examination form, measured results, disease history, medical record and/or prescription record to a medical specialist; purchasing medicine according to a medical prescription obtained after medical examination by a medical specialist; payment of remote medical diagnosis service charge using electronic cash, a credit card, a cash card or an electronic medical card.

As described above, the bio-disc can be used as a medical examination device for easily conducting remote medical diagnosis by a user at home. The bio-disc, the bio-disc drive and the remote medical diagnostic process have been described in detail in Korean Patent Application Nos. 10-2005-036983, 10-2005-0038765, 10-2005-0128469, 10-2007-0040657 and 10-2006-0073597, which were filed in the name of the present applicant and the entire disclosures of which are incorporated herein by reference.

The bio-keyboard may include a tray on which a bio-disc is horizontally loaded, a motor to rotate the loaded bio-disc, and a bio-disc drive to control the same. With recent tendency of slimming a user computer, the disc drive is generally manufactured in a vertical loading form. However, for vertical loading, it may be difficult to control fluid flow since gravity activates perpendicular to the fluid in the bio-disc. Therefore, the remote medical diagnostic device according to one embodiment of the present invention may have a bio-disc drive in a horizontal loading form enabling horizontal loading of a bio-disc or an optical disc inside a bio-keyboard. In this regard, the bio-disc drive may suitably overcome a demand for slimming a user computer. The user may conduct remote medical diagnosis by substituting the existing computer keyboard with the bio-keyboard, without replacement of a whole body of the computer. In addition, without turning on a power of the computer body, the bio-keyboard and an output device, for example, a monitor are turned on in order to drive the bio-disc derive, thus activating the optical disc or the bio-disc.

The bio-keyboard may further include at least one selected from a group consisting of a power on/off button of the bio-disc drive, a play button, a stop button, and a navigation button.

The bio-keyboard may also include a slot for inserting/ejecting a bio-chip, and a bio-chip analyzer to measure a response signal of the bio-chip and read response results thereof. The bio-chip refers to a device for various analytic performances, including: diagnostic analysis for various diseases; nucleic acid hybrid analysis; biomaterial analysis; body constitution analysis of patients for personalized medicine; urine analysis; blood analysis; environmental pollution analysis; biochemical analysis; immunological analysis, and the like. For instance, the bio-chip may include a DNA chip, a Lab-on-a chip, a protein chip, a rapid test kit and/or a test strip. Accordingly, the bio-keyboard may include a bio-analyzer, that is, the foregoing bio-disc drive and a bio-chip analyzer.

The bio-keyboard may further have at least one camera to capture images of a user in real time.

The bio-disc drive built in the bio-keyboard may play and drive general optical discs such as a DVD, CD, CD-R, CD-RW, DVD-R, etc.

The bio-keyboard may also include input/output ports for video and audio use, in order to output playback signals of an optical disc and/or input signals to be recorded.

The bio-keyboard may further include a power switch for power on/off of the bio-keyboard and the bio-mouse, wherein the power of the bio-keyboard is on/off controlled when the power of the user computer is off, while the same may be continuously turned on when the power of the user computer is on. For example, the bio-keyboard may play and drive general optical discs such as DVD, CD, CD-R, CD-RW, DVD-R, etc., thus being used as a stand-alone type DVD player even if the power of the user computer is not on.

The bio-keyboard may also include: a wired or wireless telecommunication part to receive measured signals of a medical examination device transmitted from the bio-mouse and transmit/receive data between the bio-mouse and the bio-keyboard; and a digital signal processing part to calculate measured data by processing the measured signals through a signal processing algorithm and store the calculated results in the user computer. The wireless telecommunication part may be Bluetooth-based.

The bio-keyboard may also include a winder for winding an earphone cable and a winding switch for the same. The bio-keyboard may have the winder inside the bio-keyboard to wind the earphone cable, while releasing and using the same with a desired length for use.

The bio-keyboard may further include a card reader for payment of a service charge for remote medical examination or a medical coupon card reader. A card insertion part or a card slot of the card reader may be formed at a site on a periphery of the bio-keyboard.

An electrode to measure body fat or electrocardiogram of the human and/or a pressure sensor to measure blood pressure and pulse may be provided at both sides of the bio-keyboard. The body fat measurement electrode may use bio-electrical impedance analysis (BIA) wherein both hands contact the electrode, in order to determine a body fat fraction contained in a particular site of the body of a subject.

The remote medical diagnostic device according to the embodiment of the present invention may be permanently placed in a user computer and include a CPU to provide GUI to a user.

The GUI may drive and control the bio-mouse and the bio-analyzer described above, and convert data input from a medical examination device in the bio-mouse as well as the bio-analyzer into numerical values via an analysis program, and output the converted values, in turn enabling remote medical diagnosis through Internet.

The GUI may transmit bar codes of the bio-disc provided from the bio-mouse or the bio-analyzer, ID number of the bio-disc, ID number of the bio-disc drive, animal RF ID, or measured data of the medical examination device to a remote server via Internet.

The GUI may further have a button for selecting a desired one among multiple medical examination devices.

The GUI may have multiple functions including: displaying measured results of the bio-analyzer or the medical examination device in any one of a graphic mode or a high-middle-low level mode; displaying diagnosis results of the bio-analyzer or the medical examination device; demonstration of a medical examination form; description of Q and A; displaying conditions of the bio-analyzer or the medical examination device used by a user in real time; demonstration of payment of service charge; exhibition of medical data or medicine prescription provided by a doctor, and so forth.

The GUI may further have a control right assignment button to transfer the remote control right of the GUI and the medical examination device to a remote doctor. The assignment of control right may enable the doctor to monitor behavior of the bio-analyzer or the medical examination device in real time or to directly and remotely transmit an instruction of controlling behavior of the bio-analyzer or the medical examination device to a user computer.

The GUI may be automatically activated and displayed on an output device of the user computer in a medical examination mode.

The GUI may perform authentication of the bio-mouse by sending a product ID of the bio-mouse stored in a memory of the bio-mouse to a remote diagnosis server.

The GUI may transmit bar codes of the bio-disc provided from the bio-mouse or the bio-keyboard, ID number of the bio-disc, ID number of the bio-disc drive, animal RF ID, or measured data of the medical examination device to a remote server via Internet. In addition, the GUI may further include a specific animal recognition software which transmits an animal RF ID to an animal ID management server and executes identification of a subject animal.

The GUI may include at least one function selecting button, which is selected from a group consisting of an analysis starting button for control of the bio-analyzer or the medical examination device, an analysis stopping button, a power on/off button, an eject (unloading) button, a remote transmission button, a remote reception button, a button for confirmation of diagnosis results, a button for confirmation of diagnosis and medical records, a medical examination form button, Q&A button, a button for confirmation of payment information and a payment approval button. For example, using the eject button, a bio-disc or a bio-chip loaded in the bio-analyzer may be ejected.

By clicking the remote transmission button after completion of analysis using the bio-analyzer or the medical examination device, the GUI may transmit medical data, a medical examination form, or medical questions prepared by a user to a doctor.

The GUI may also include fingerprint recognition software, in order to automatically identify the user. For this purpose, the bio-mouse or the bio-keyboard may further have a fingerprint recognition system.

According to one exemplary embodiment of the present invention, there is provided a remote medical diagnostic method which includes: preparing the foregoing remote medical diagnostic device; connecting a user computer of the diagnostic device to a web site that provides remote medical diagnosis service; accessing a virtual doctor or a remote doctor who provides the foregoing remote medical diagnosis service; operating the bio-analyzer or the medical examination device in the foregoing diagnostic device in order to detect measured signals according to instruction of the virtual doctor or the remote doctor; processing the measured signals to prepare data; and transmitting the measured data to the virtual doctor or the remote doctor.

The remote medical diagnostic method according to the exemplary embodiment of the present invention includes, in particular, provision of the remote medical diagnostic device according to the embodiment of the present invention. Such a remote medical diagnostic device was previously described above.

The remote medical diagnostic method according to the exemplary embodiment of the present invention also includes connection of a user computer in the remote medical diagnostic device to a web site providing a remote medical diagnosis service.

The website connection may also include a step of membership application for the subject website. The membership application step may further include an ID and password setup step.

A step of reading at least one product ID selected from a group consisting of ID of the bio-disc, ID of the bio-disc drive, ID of the bio-keyboard, ID of the bio-mouse and ID of each medical examination device built in the bio-mouse may be additionally included in the foregoing website connection. The product ID reading step may also include an authentication step of the product ID by transmitting the product ID to the subject website. If desired software corresponding to the product ID is not contained in the GUI, another step of directly downloading the desired software via Internet and upgrading the user computer may be further included.

The remote medical diagnostic method according to the exemplary embodiment of the present invention includes, in particular, medical examination by a virtual doctor wherein the virtual doctor guides a procedure of using the bio-analyzer or the medical examination device during use thereof or, when monitoring and finding errors in use, requests the user to correct the error. Alternatively, medical examination by a remote doctor wherein the remote doctor guides a procedure of using the bio-analyzer or the medical examination device during use thereof or, when monitoring and finding errors in use, requests the user to correct the error, may be further included in the remote medical diagnostic method.

The remote medical diagnostic method according to the exemplary embodiment of the present invention may include processing of measured signals to prepare data. The remote medical diagnostic method according to the exemplary embodiment of the present invention may also include displaying of the measured data on a monitor screen.

The remote medical diagnostic method according to the exemplary embodiment of the present invention may include remote transmission of the measured data to a remote doctor. Alternatively, the measured data may be transmitted to a virtual doctor as well as the remote doctor.

The remote medical diagnostic method according to the exemplary embodiment of the present invention may further include switching the bio-mouse to a medical examination mode using a mode selection switch.

The remote medical diagnostic method according to the exemplary embodiment of the present invention may also include assignment of GUI control right to transfer the control right to a remote doctor.

The remote medical diagnostic method according to the exemplary embodiment of the present invention may additionally include a marker location tracking step to trace a position or orientation of the bio-mouse.

The remote medical diagnostic method according to the exemplary embodiment of the present invention may include medical examination by a virtual doctor. In particular, such medical examination executed by the virtual doctor may include at least one process selected from a group consisting of: recognizing the body of a user via a camera and demonstrating a real-time mimesis graphic of the user body, which was obtained by graphic processing using a 2- or 3-dimensional animation tool or a virtual reality tool, on a monitor screen; generating voice commands in sequential order based on steps of use and orders of multiple medical examination devices, in order to instruct the user on how to use those medical examination devices through a speaker; superimposing symbols of the real-time mimesis graphic, in order to instruct the user on how to use the medical examination devices; expressing behavior of the user or executing mimesis thereof in real time while monitoring use conditions of the medical examination devices by the camera; demanding correction of errors while monitoring use conditions of the medical examination devices by the camera and expressing behavior of the user or executing mimesis thereof in real time; superimposing different symbols of the real-time mimesis graphic on position information of the presently used medical examination device and standard medical examination position information, in order to provide specific information to the user in real time, wherein the user can recognize a degree of leaving the standard medical examination position from the specific information; storing the measured data metered by the medical examination device or transmitting the same to a remote medical diagnosis server; and conducting self-analysis of the metered data from the medical examination device by medical examination software and notifying the user of diagnosis results.

The foregoing symbols may include additional character explanation, cursor, arrow, numerals, special symbols and characters and/or blinking markers to indicate the same. The camera may include one at left side, one at right side, one at top side and the last one at bottom side. Using only a camera, little perspective information is obtained. Accordingly, by arranging multiple cameras at right and left, and top and bottom sides, it is possible to obtain three-dimensional images of an object and to effectively monitor use conditions and/or behavior of the medical examination device in three-dimensional order. As to the foregoing process, a well-known triangulation technique is mainly used. The cameras may comprise a visible camera, an infrared camera or a fluorescent camera. The bio-mouse may have at least one special marker attached thereto or be painted. Such a special marker may be sensed by the camera described above, and be suitable for video tracking, motion tracking, capture and setup of standard coordinates, recognition of the bio-mouse and segmentation, etc. Recognition of the bio-mouse may be performed by object recognition technique, and object recognition and segmentation are well known in the related art. The special marker may comprise, for example, paints such as luminescent paint or fluorescent paint, or at least one LED. Using the special marker, position and/or orientation of the medical examination device on a three-dimensional space may be identified. Also, accumulation tracking of the location of the special marker over time may enable real time tracing or monitoring of conditions of the medical examination device used by a user.

The animation tool described above includes graphic tools such as OPENGL, 3D Studio MAX, etc., which are well known in related art.

With regard to the remote medical diagnostic method according to the exemplary embodiment of the present invention, if GUI does not have software including medical software that has protocol and analysis algorithms corresponding to each of the medical examination devices, downloading the desired driver software on Internet and upgrading the user computer may also be included in the diagnostic method.

The remote medical diagnostic method according to the exemplary embodiment of the present invention may further include medical examination by the remote doctor. Such medical examination executed by the remote doctor may include at least one process selected from a group consisting of: recognizing the body of a user via a camera and transmitting the recognized images in real time to the remote doctor or demonstrating the same on a monitor screen; generating voice commands in sequential order based on steps of use and orders of multiple medical examination devices by the remote doctor, in order to instruct the user on how to use those medical examination devices through a speaker; superimposing instruction cursors provided by the remote doctor on the monitor screen, in order to instruct the user on how to use the medical examination devices; demanding correction of errors while monitoring use conditions of the medical examination devices by the camera; storing the measured data metered by the medical examination device or transmitting the same to a remote medical diagnosis server and the remote doctor; and conducting analysis of the metered data from the medical examination device by the remote doctor and notifying the user of diagnosis results through a message transfer tool.

The remote medical diagnostic method according to the exemplary embodiment of the present invention may further include medical self-examination by a user. Such medical self-examination executed by the user may include: recording use conditions of the medical examination device used by the user by recognizing the same using a camera, recording and storing the recognized results; transmitting the measured data metered by the medical examination device and results of recording the use conditions to the remote doctor as well as a remote medical diagnosis server; and analyzing the metered data and the recorded results of the use conditions by the remote doctor and notifying the user of diagnosis results via a message transfer tool.

Advantageous Effects

As described above, the remote medical diagnostic device and a diagnostic method using the same according to embodiments of the present invention may be effectively used in remote medical diagnosis.

DESCRIPTION OF THE DRAWINGS

These and/or other aspects of the invention will become apparent and more readily appreciated from the following description of the embodiments, taken in conjunction with the accompanying drawings of which:

FIGS. 2 and 3 illustrate a bio-mouse according to one embodiment of the present invention; and FIGS. 4 to 9 illustrate examples of a GUI providing remote medical diagnosis service by the remote medical diagnostic device according to the embodiment of the present invention.

MODE FOR INVENTION

Now, preferred embodiments of the present invention will be explained with reference to the accompanying drawings.

Figure 1:
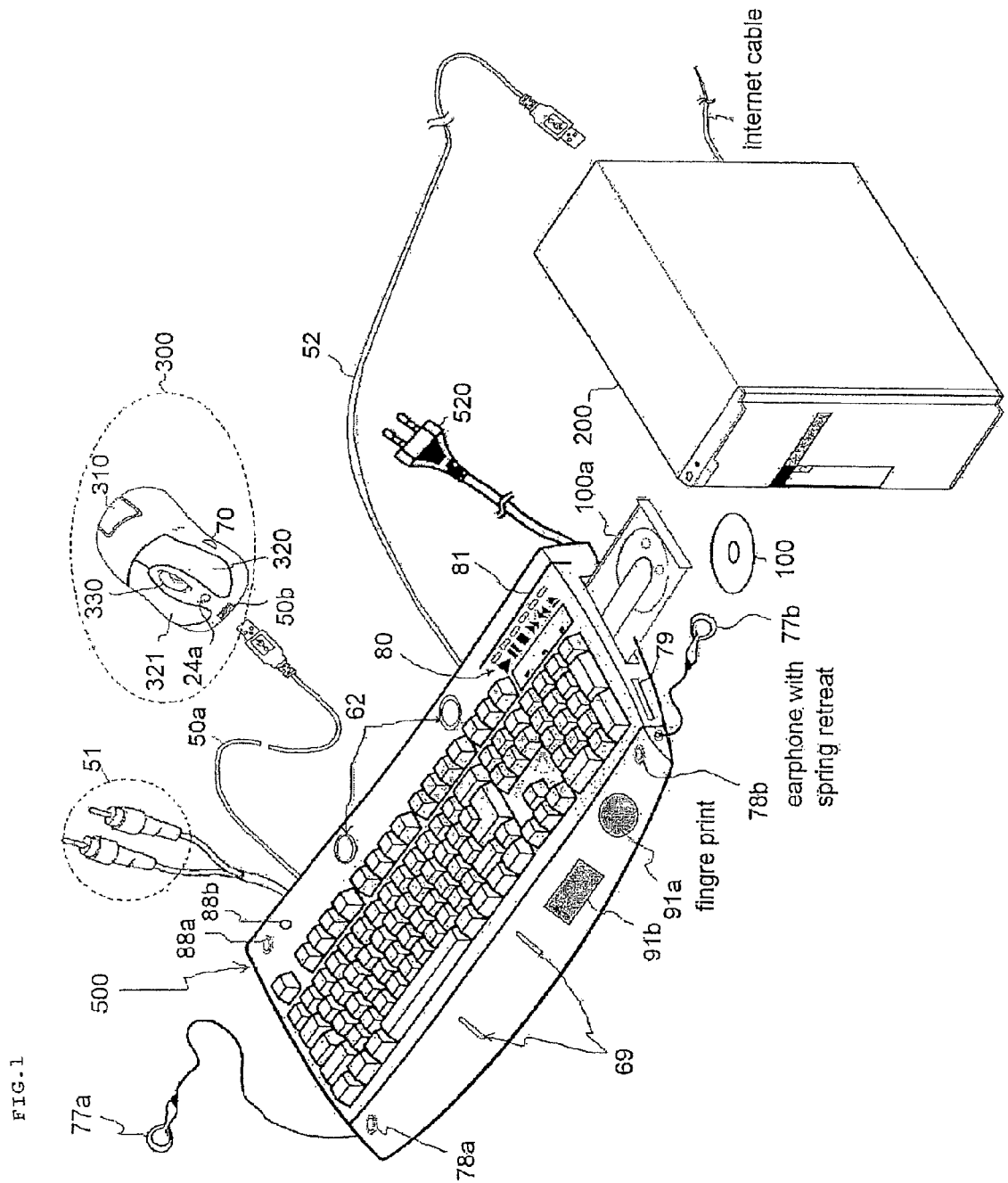
FIG. 1 illustrates a remote medical diagnostic device including a bio-mouse and a bio-keyboard according to one embodiment of the present invention.

FIG. 1 illustrates a remote medical diagnostic device including a bio-mouse and a bio-keyboard, according to one embodiment of the present invention.

The remote medical diagnostic device includes a user computer 200; a bio-mouse 300; a bio-disc drive 100a; and a bio-keyboard 500.

The user computer 200 is connected to a wired or wireless Internet and can request medical services, for example, medical consultant services or transmit and/or receive measured medical results. The user computer 200 may have a system providing a graphical user interface (GUI) or be connected to the same.

The bio-mouse 300 may include various medical examination devices and an optical mouse part. The medical examination devices may be, for example: a temperature sensor that senses body temperature of a user and generates a sensing signal corresponding to the sensed temperature; an ultrasound sensor for ultrasound test; a stethoscope sensor to listen to abnormal heart sound of a patient; a blood pressure sensor to receive a blood pressure measurement signal; and a wireless transmission/reception sensor to send and receive information of a capsule endoscope. The remote medical diagnostic device according to one embodiment of the present invention includes at least one medical examination device selected from a group consisting of: a temperature sensor to sense body temperature of a user and generate a sensing signal corresponding to the same; an image sensor for oral test; a ultrasound sensor for ultrasound test; a stethoscope sensor to auscultate abnormal heart sound of a patient; a blood pressure sensor to receive a blood pressure measurement signal; a wireless transmission/reception sensor to transmit and receive information of a capsule endoscope.

Numeral 24a in the drawings means a marker, which is attached to both a top face 24a and a bottom face (not shown) of the bio-mouse 300, enabling video tracking, motion tracking or capture, and standard coordinate setup or recognition of a medical examination device. Using the marker, a position and an orientation of the bio-mouse 300 in three-dimensional space may be identified and, by accumulatively tracking a location of the marker over time, conditions of the medical examination device used by the user may be monitored in real time.

The bio-disc drive 100a may drive and control the bio-disc 100 for analysis of samples.

The bio-keyboard 500 includes a general computer keyboard to input information to the user computer. The bio-keyboard 500 may have the foregoing bio-disc drive 100a. The bio-disc drive 100a can drive a common optical disc simultaneously with the foregoing bio-disc. The bio-keyboard has an input/output port 51 for video and audio devices to output playback signals or input recording signals of the common optical disc. The input/output port 51 for video and audio devices may support, for example, digital image, component image, S-VHS, and various other image formats.

Numeral 80 in the drawings means a playback button to drive the bio-disc or the optical disc, a stop and pause button, a search button and/or an eject button.

Numerals 78a and 78b refer to start switches for winding earphone cables 77a and 77b.

Numeral 79 means a slot for inserting/releasing a bio-chip.

Numeral 62 indicates a camera for real time capturing images of the user, wherein two cameras are placed at the left side and right side of the bio-keyboard 500, respectively, in order to capture three-dimensional images of an object, thus monitoring conditions of the medical examination device used by the user and behavior of the same in the three-dimensional mode.

Numeral 81 indicates a card insertion part or a card slot of a card reader for payment of remote medical examination service charge. In this regard, a handwritten signature may be recorded on an LCD signature input part 91b.

Numeral 50b refers to a USB connector to connect the bio-mouse 300 with the bio-keyboard 500 via a USB cable 50a. Numeral 52 is another USB cable to connect the bio-keyboard 500 with the user computer 200. The USB cables 50a and 52 may be replaced by Bluetooth capable of wirelessly transmitting information. The measured signal obtained from the medical examination device of the bio-mouse 300 is transmitted to a digital signal processor (not shown) in the bio-keyboard by Bluetooth, thus outputting or storing the measured data.

Numerals 88a and 88b are a power switch and a power LED of the bio-keyboard 500 for turning on/off the power provided through a power cable 520. In this case, the power of the bio-keyboard 500 may be turned on/off independently of the power of the user computer 200. Therefore, the bio-keyboard 500 can replay or drive any common optical disc (DVD, CD, CD-R, CD-RW, DVD-R, etc.) without turning on the power of the user computer, and may also function as a stand-alone type DVD player.

Numeral 69 is an electrode to measure body fat or electrocardiogram of the human, for example, a user, or a pressure sensor to measure blood pressure or pulse of the user.

The bio-keyboard 500 of the remote medical diagnostic device according to one embodiment of the present invention may on/off control the power of the bio-keyboard only when user authentication is obtained by a fingerprint recognition system 91a. Herein, the bio-keyboard is not powered by others except for the identified user, thus preventing unauthorized use of the user computer by any third party.

Figure 3:
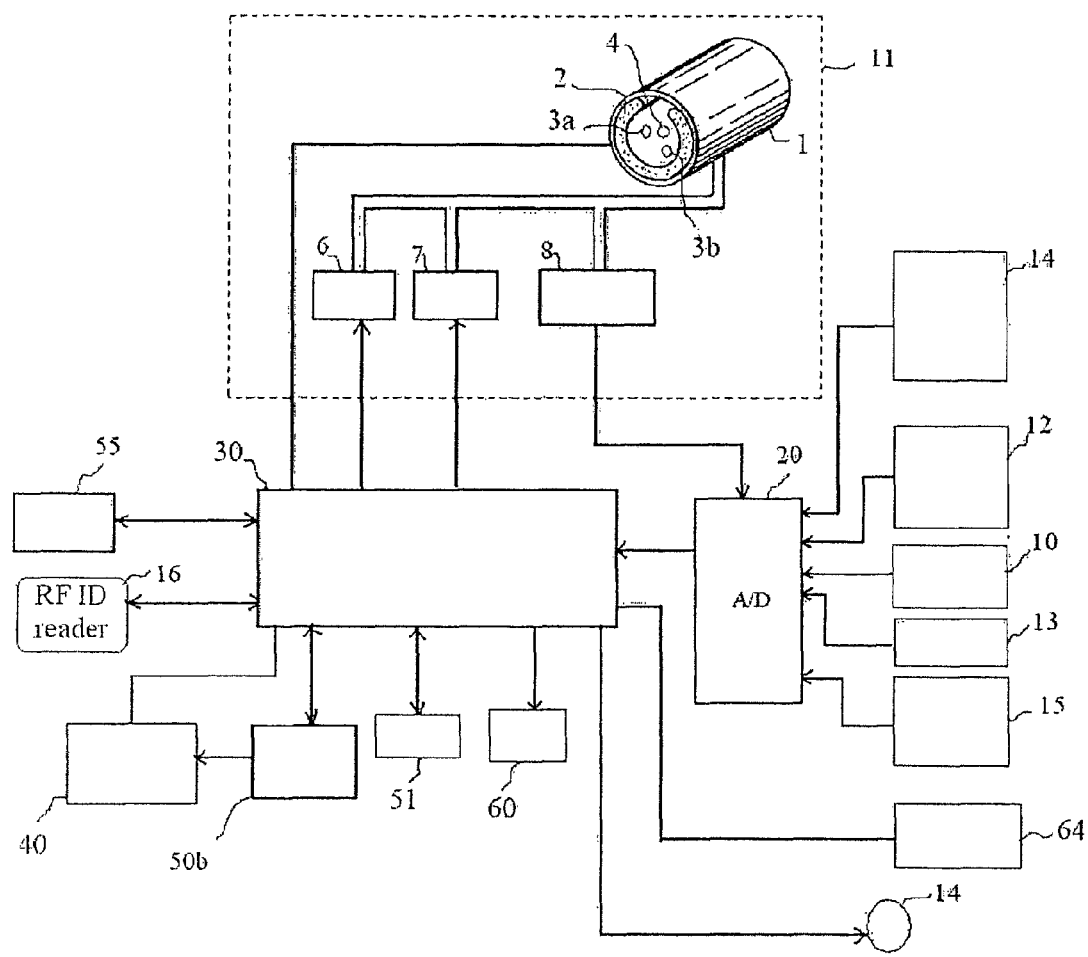

FIGS. 2 and 3 illustrate an example of the bio-mouse 300 according to the embodiment of the present invention.

The bio-mouse 300 may have at least one medical examination device selected from a group consisting of a temperature sensor 10 to sense body temperature of a user and generate the sensed signal, an image sensor 12 for oral test, a ultrasound sensor 14 for ultrasound test, a stethoscope sensor 13 to auscultate a patient's heart, a blood pressure sensor 11 to obtain measured signal of the blood pressure, and a wireless transmission/reception sensor 15 to transmit and receive information of a capsule endoscope, as well as an optical mouse part 64 of a computer.

Numeral 330 is a mouse wheel and numerals 320 and 321 indicate left and right mouse buttons, respectively. The bio-mouse 300 has a finger hole 310, into which a finger connected to the finger cuff 1 of the blood pressure sensor 11 is inserted for blood pressure check, a door 311 to open and close the finger hole 310, and a start button 70 for measurement of blood pressure.

Numeral 16 is an RF ID reader to read contents of an animal RF ID or an RF IC in the bio-disc. The RF ID reader may also function as an RF generation part to supply energy to the capsule endoscope.

The blood pressure sensor 11 may have a finger cuff 1 covering a bladder 2 to be expanded by air pressure and pressurize a finger of the patient, a pressure part 6 to supply pressurized air at a preset pressure level, an air exhausting part 7 to discharge air out of the finger cuff 1 at a high or low speed during measurement of the blood pressure, a pressure signal detection part 8 to receive pulse vibration from the finger to the finger cuff 1 and convert the vibration into electric charge, a PPG signal detection part comprising an LED part 3a and an optical sensor 3b to detect PPG signals, and a temperature signal detection part 4 having a temperature sensor to detect a temperature of the finger. Moreover, the blood pressure sensor 11 may be connected to an A/D converter 20 that receives signals generated from the PPG signal detection part (3a and 3b), the temperature signal detection part 4 and the pressure signal detection part 8, and converts the received signals into digital signals. The pressure signal, the PPG signal and the temperature signal converted into the digital signals are duly transferred to the digital signal processor of the bio-keyboard, in turn estimating a blood pressure value.

The bio-mouse 300 may be attached and detached by a USB connection part 50b. The bio-mouse 300 can have a battery 40 built therein which is rechargeable when connected to the user computer 200 via USB. The USB connection part 50b may enable transmission of measured data obtained from the medical examination device of the bio-mouse by connection between the bio-mouse 300 and a mobile phone via USB terminals to a remote doctor or a computer main body, when the bio-mouse 300 is separated from the user computer 200.

The bio-mouse 300 may be connected to the bio-keyboard 500 through the USB connection part 50b or a wireless telecommunication device 51. If connecting the bio-mouse 300 via a USB cable 50a, the battery 40 may be recharged. While the bio-mouse 300 is separated from the bio-keyboard 500, this can be operated using a power of the battery 40 and the measured signal from the medical examination device of the bio-mouse 300 may be transmitted to the bio-keyboard by the wireless telecommunication device 51. The wireless telecommunication device may include Bluetooth.

Numeral 14 indicates an LED for lighting an image sensor or a multi-colored LED of a mouse wheel 330. The multi-colored LED may distinguish a general mode and a medical examination mode of the bio-mouse according to colors of the LED.

Numeral 60 refers to a permanent magnet or electromagnet functioning as a position controller of the capsule endoscope.

Numeral 55 is a memory part temporally storing a measured signal of the medical examination device of the bio-mouse 300, wherein the signal was converted into a digital signal by the A/D converter.

Numeral 30 is a central processing unit (CPU) to control respective parts of the bio-mouse 300.

Figure 4:
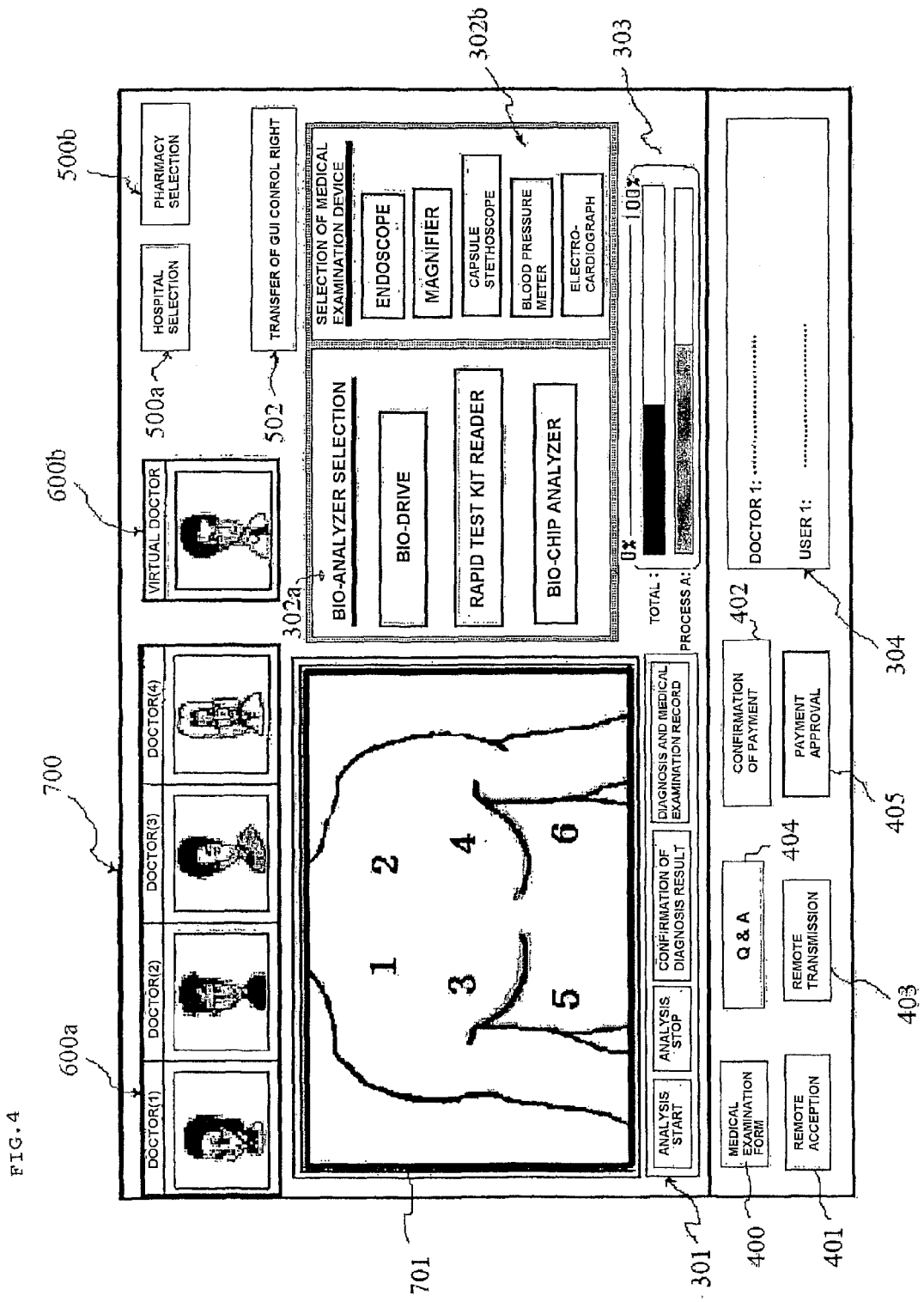
Figure 5:
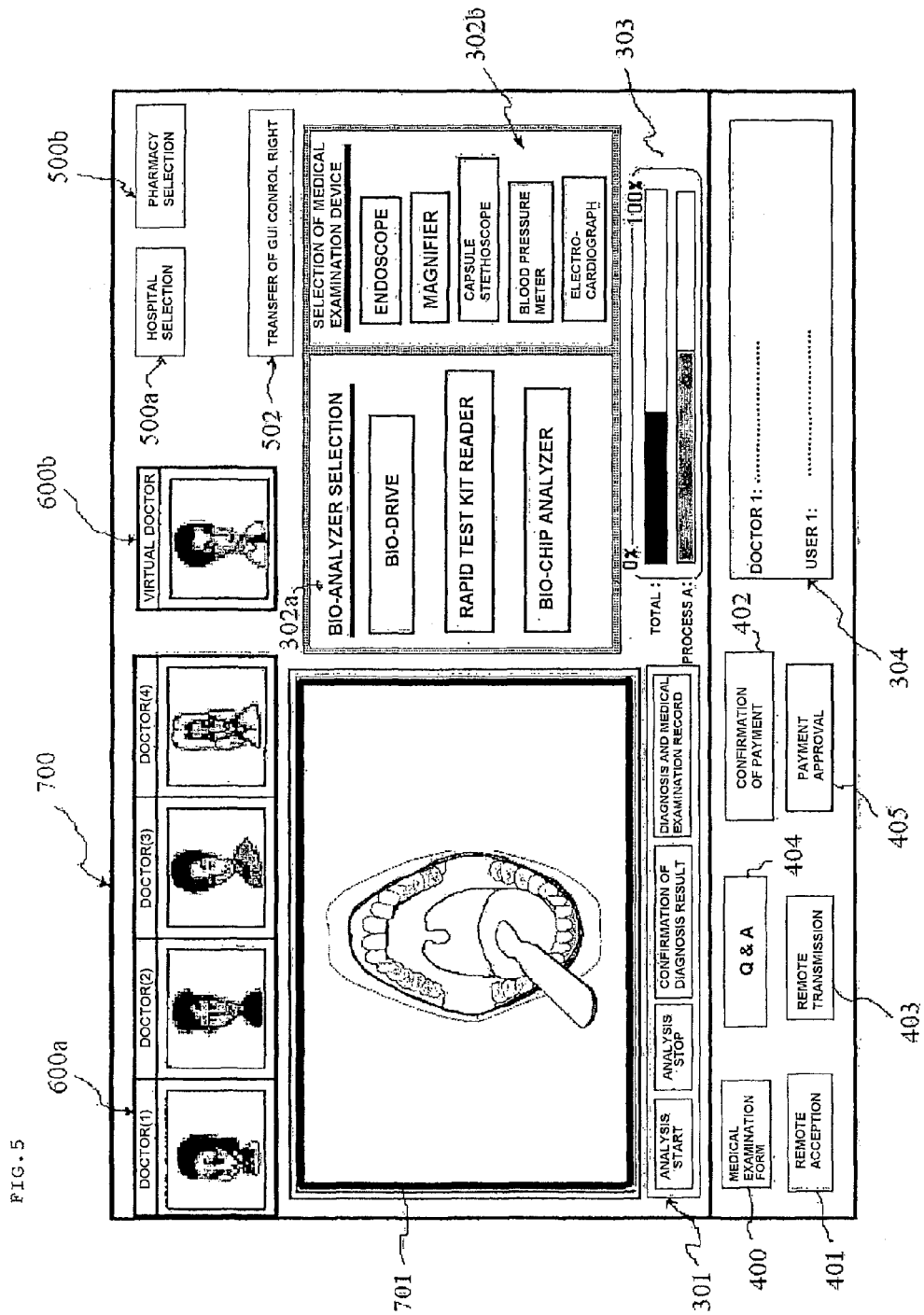
Figure 6:
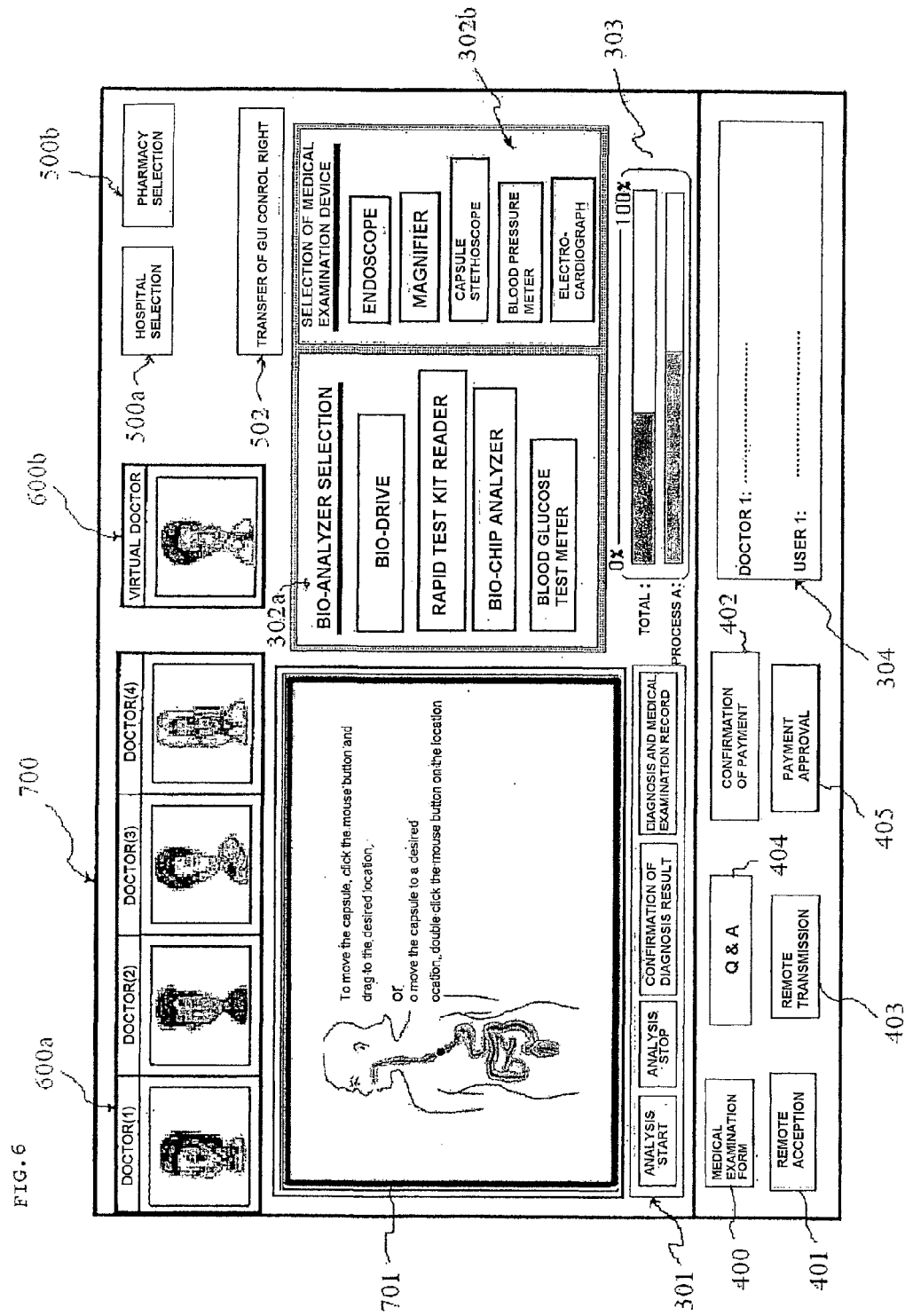

FIGS. 4 to 6 illustrate particular examples of the GUI wherein a remote medical diagnosis service is provided by the remote medical diagnostic device according to one embodiment of the present invention.

The GUI 700 comprises different buttons and windows to enable a user to easily approach the remote medical diagnostic device.

Numeral 301 is a button panel including function selection buttons while numeral 303 is a display window showing a rate of analysis progress by the bio-analyzer.

Numeral 302a means a panel including different buttons for selecting one of multiple bio-analyzers, and numeral 302b indicates another panel including different buttons for selecting one of multiple medical examination devices. Numeral 304 refers to a character chat window for text conversation.

The GUI 700 may monitor in real time conditions of behavior of the bio-analyzer connected to the user computer 200 and/or progress thereof through a wired or wireless telecommunication device between the user computer 200 and the bio-analyzer, or transport control commands to the bio-analyzer in order to directly control behavior of the bio-analyzer. Briefly, the GUI 700 can generate control commands for driving the bio-analyzer at constant time intervals according to corresponding protocols and transmit the commands to the bio-analyzer, when a start button in the button panel 301 is clicked after confirming connection of the bio-analyzer with the user computer 200 and as to whether a bio-disc or a bio-chip was loaded in the bio-analyzer. Furthermore, the GUI 700 may receive measured data from the bio-analyzer after the bio-analyzer completes analysis.

Numeral 701 is a medical service window showing measured data of the bio-analyzer in a numeral, a graph or a high-middle-low level mode, measured data of the medical examination device in a numeral, a graph or a high-middle-low level mode, a diagnosis result obtained using the bio-analyzer or the medical examination device, a medical examination form or Q & A; displaying use conditions of the bio-analyzer or the medical examination device in a real time mimetic graphic form, use procedures of the bio-analyzer or the medical examination device, payment of medical service charge; or demonstrating medical data or drug prescription obtained by the doctor and providing the same to the user.

Furthermore, the GUI 700 may further include: a remote transmission button 403 to store measured data of the bio-analyzer, a medical examination form, Q&A, information regarding details of diagnosis or medical data during remote diagnosis, etc. in a remote diagnosis server or to transmit the same to a remote doctor; a remote reception button 401 to receive diagnosis results, a medical prescription, a medical examination form, Q&A, medical data or specification of payment from the remote diagnosis server or the doctor; a payment confirmation button 402 to check specification of the payment; a payment approval button 405 to allow payment of remote diagnosis service charge using an electronic cash, a payment card or by pushing mobile phone buttons; a medical examination form button 400 to edit the form or display the same; a Q&A button 404 to prepare or display Q&A; a doctor selection window 600a or 600b to select a desired doctor; a hospital selection button 500a and a pharmacy selection button 500b to select desired hospital and pharmacy; and a control right assignment button 502 to transfer the remote GUI control right to the selected doctor.

When the remote control right of GUI 700 was assigned to the selected doctor, the doctor can remotely control the GUI 700 of the user computer 200 and, in this case, remote medical diagnosis service using the bio-analyzer or the medical examination device may be conveniently provided by the doctor having the remote control right, although the user does not know a procedure of using the GUI 700. Herein, even if the remote control right is transferred to the doctor, payment approval right is still owned by the user.

FIG. 4 illustrates one example of the remote medical diagnosis service provided to a user when the user selected a stethoscope sensor among various medical examination devices.

The GUI may have different functions, for example: imaging the body of a patient using a camera and superimposing symbols on the images of the patient body to indicate a standard medical examination site, to which a stethoscope sensor should be located, to the user through the medical service window 701; indicating a standard medical examination site in a mimetic graphic mode, to which the stethoscope sensor should be located, to the user through the medical examination window 701; or superimposing a directed cursor obtained in real time from the doctor on the images of the patient body to indicate the standard medical examination site, to which a stethoscope sensor should be located, to the user through the medical service window 701 or to instruct the user as to a procedure of using a desired medical examination device, and the like. The foregoing symbol may include, for example, additional descriptive texts, indication lines, cursors, arrows, numerals, special symbols or characters, and blinking motion thereon. FIG. 4 illustrates one example of a process of indicating standard medical examination sites and orders exhibited by numerals such as 1, 2, 3, 4, 5 and 6 as the foregoing symbol to the user, through the medical service window 701.

The GUI 700 may simultaneously demonstrate a procedure of using the medical examination device to the user with video images and voice. For example, the GUI 700 can introduce a procedure of using the medical examination device to the use by a mimetic graphic (animation image) and a voice explanation synchronized with the graphic or by voice instruction of a doctor provided in real time by the doctor, through the medical service window 701.

Simultaneously, the medical service window 701 of the GUI 700 can be viewed in real time by the doctor via a computer of the doctor.

FIG. 5 illustrates one example of the remote medical diagnosis service provided to a user when the user selects a magnifier among various medical examination devices. In particular, the medical service window 701 demonstrates oral conditions observed by an image sensor.

FIG. 6 illustrates one example of the remote medical diagnosis service provided to a user when the user selected a capsule endoscope among various medical examination devices. In particular, the medical service window 701 demonstrates the present location of the capsule endoscope as well as an inner part of the body of the user. The capsule endoscope moves around inside the body and transmits images captured at respective sites of the body to the user computer 200 via a wireless transmission/reception sensor and, therefore, the doctor can observe the captured images in real time.

Figure 7:
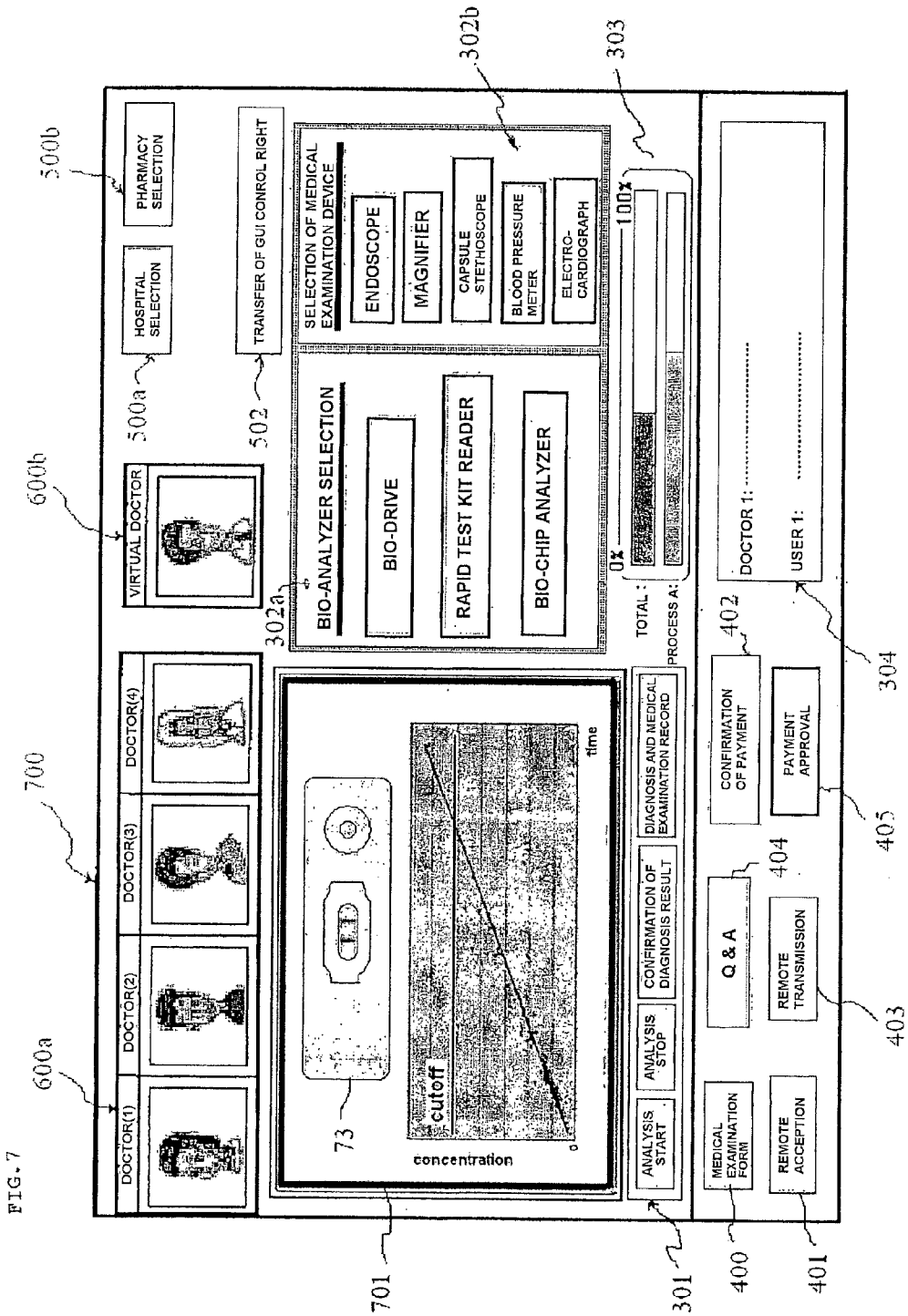
Figure 8:
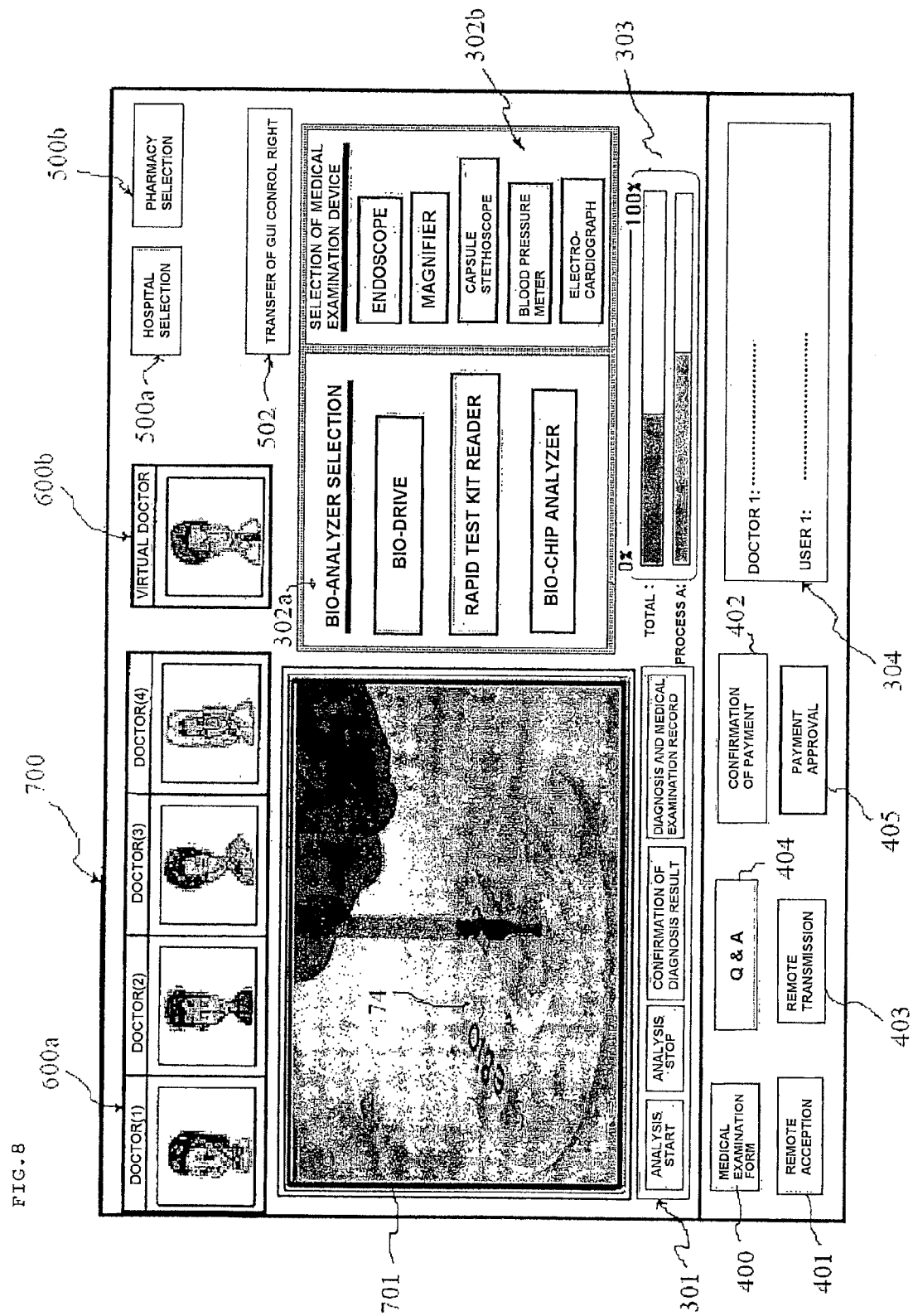

FIGS. 7 to 9 illustrate respective examples of the GUI providing remote medical diagnosis service by the bio-analyzer according to one embodiment of the present invention.

FIG. 7 illustrates one example of the remote medical diagnosis service provided to a user when the user selects a rapid test kit reader (RTKR) among various bio-analysis devices. The medical service window 701 demonstrates measured data of the RTKR as well as previously accumulated data, in a graph mode together with a cutoff value. The accumulated data enables observation of change in disease, and tracking and maintenance thereof, thus contributing to early detection of diseases and reducing diagnostic error rate.

FIG. 8 illustrates one example of the remote medical diagnosis service provided to a user when the user selects a bio-disc drive among various bio-analysis devices. The medical service window 701 demonstrates in real time a process of injecting a blood sample onto the bio-disc by the user to a remote doctor.

FIG. 9 indicates measured data obtained from the bio-analyzer on the medical service window 701, in order to demonstrate the measured data to the user and the doctor.

Although a few exemplary and preferred embodiments of the present invention have been shown and described, it would be appreciated by those skilled in the art that various changes and modifications may be made in these embodiments without departing from the principles and spirit of the invention, the scope of which is defined in the claims and their equivalents.

The invention claimed is:

1. A remote medical diagnostic device, comprising:
   a user computer connected to a wired or wireless internet to send and/or receive information regarding medical services;
   a bio-mouse connected to the user computer via a wired or wireless network, which includes at least one medical examination device selected from a group consisting of a temperature sensor, an image sensor, a ultrasound sensor, a stethoscope sensor, a blood pressure sensor and a wireless transmission/reception sensor to send/receive information of a capsule endoscope, as well as an optical mouse part;
   a bio-keyboard including a computer keyboard, a tray on which a bio-disc or optical disc may be horizontally loaded, a motor for rotating the loaded bio-disc or optical disc, and a bio-disc drive to control the same; and
   a central processing unit (CPU) providing a graphic user interface (GUI) to the user.

2. The diagnostic device according to claim 1, wherein the bio-disc comprises at least one device selected from a group consisting of a disease diagnostic analyzer, a nucleic acid hybrid analyzer, a biomaterial analyzer, a body constitutional analyzer for personalized medicine, a urine analyzer, a blood analyzer, an environmental pollution analyzer, a bio-chemical analyzer and an immunological analyzer.

3. The diagnostic device according to claim 1, wherein the bio-mouse includes at least one device selected from a group consisting of a selection switch to select a general mode or a medical examination mode, at least two light receiving lenses to switch light receiving characteristics according to the general mode and the medical examination mode, and a mouse wheel having a multi-colored LED to display the general mode and the medical examination mode.

4. The diagnostic device according to claim 1, wherein the bio-mouse further includes a position control device to control a position and a posture of the capsule endoscope inside the human body or an RF generation part to supply energy to the capsule endoscope.

5. The diagnostic device according to claim 4, wherein the position control device is a permanent magnet or electromagnet.

6. The diagnostic device according to claim 1, wherein the bio-mouse further includes a marker for tracking a position or an orientation of the bio-mouse.

7. The diagnostic device according to claim 1, wherein the bio-mouse further includes an RF ID reader to read an RF ID or contents of an RF IC contained in the bio-disc.

8. The diagnostic device according to claim 1, wherein the bio-mouse further includes a memory to store production information including version, production year and production ID of the bio-mouse as well as the data obtained from the medical examination device.

9. The diagnostic device according to claim 1, wherein the bio-keyboard further includes a memory to store product information including version, production year and production ID of the bio-keyboard as well as the data obtained from the bio-mouse.

10. The diagnostic device according to claim 1, wherein the blood pressure sensor includes a finger hole into which a finger is inserted for blood pressure check, a door to open and close the finger hole, and a finger cuff to apply pressure to a finger in right and left and/or up and down directions.

11. The diagnostic device according to claim 10, wherein the blood pressure sensor comprises: a photoplethysmographic (PPG) signal detection part which includes a pressurizing part to feed pressurized air at a preset pressure level for the finger cuff, an air exhausting part to discharge air out of the finger cuff at a high or low speed during measurement of blood pressure, a pressure signal detection part to receive pulse vibration transferred from a finger to the finger cuff and to convert the vibration into electric charge, an LED part to detect PPG signal, and an optical sensor; and a temperature signal detection part to detect a temperature signal of the finger using the temperature sensor.

12. The diagnostic device according to claim 1, wherein the bio-keyboard further includes at least two cameras to capture images of the body of the user in real time.

13. The diagnostic device according to claim 1, wherein the bio-keyboard further includes an input/output port for video and audio systems to output a playback signal of an optical disc or input a signal to be recorded.

14. The diagnostic device according to claim 1, further comprising a playback button to drive the bio-disc or the optical disc, a stop and pause button, a navigation button and an eject button.

15. The diagnostic device according to claim 1, wherein the bio-keyboard further includes an input/output port for video and audio systems to output playback signal of the optical disc or to input a signal to be recorded.

16. The diagnostic device according to claim 1, wherein the bio-keyboard further includes a power cable to supply power to the bio-keyboard, a power switch to turn on/off the power of the bio-keyboard independent of a power of a main body of the user computer, and a power LED to display power condition of the bio-keyboard.

17. The diagnostic device according to claim 1, wherein the bio-keyboard further includes: a wired or wireless telecommunication part that receives a measured signal transmitted from the medical examination device of the bio-mouse or transmits/receives data between the bio-mouse and the bio-keyboard; and a digital signal processor that processes the measured signal using a signal processing algorithm to calculate data and displays the result on the user computer or stores the same.

18. The diagnostic device according to claim 1, wherein the bio-keyboard further includes a slot through which a bio-chip is inserted and ejected and a bio-chip analyzer to measure a response signal of the bio-chip and read the response result.

19. The diagnostic device according to claim 1, wherein the bio-keyboard further includes an electrode to measure body fat or electrocardiogram at each side of the bio-keyboard, or a pressure sensor to measure blood pressure and pulse.

20. A remote medical diagnostic method, comprising:
preparing the remote medical diagnostic device according to claim 1;
connecting a user computer of the diagnostic device to a web site that provides a remote medical diagnosis service;
accessing a virtual doctor or a remote doctor that provides the foregoing remote medical diagnosis service;
operating the bio-analyzer or the medical examination device in the foregoing diagnostic device in order to detect measured signals according to instruction of the virtual doctor or the remote doctor;
processing the measured signals to prepare data; and
transmitting the measured data to the virtual doctor or the remote doctor.

21. The diagnostic method according to claim 20, further comprising:
reading at least one product ID selected from a group consisting of, ID of the bio-disc, ID of the bio-disc drive, ID of the bio-keyboard, ID of the bio-mouse and ID of each medical examination device in the bio-mouse.

22. The diagnostic method according to claim 21, wherein the reading of product ID further comprises transmission of the product ID to a subject website server to achieve authentication of the product ID.

23. The diagnostic method according to claim 20, wherein the measurement of signals comprises spatially shifting the bio-mouse to a desired site of the body of the user or a standard medical examination position.

24. The diagnostic method according to claim 20, wherein the measurement of signals comprises adjusting attraction or repulsion of the permanent magnet or electromagnet in the bio-mouse in order to control a position or a posture of the capsule endoscope contained in the body of the user.

25. The diagnostic method according to claim 20, further comprising assignment of remote GUI control right to a remote doctor.

26. The diagnostic method according to claim 20, further comprising a step of tracking a marker location in order to trace a position and an orientation of the marker.

27. The diagnostic method according to claim 20, further comprising at least one step selected from a group consisting of:
recognizing the body of a user via a camera and demonstrating a real-time mimesis graphic of the user body, which was obtained by graphic processing using a 2- or 3-dimensional animation tool or a virtual reality tool, on a monitor screen;
generating voice commands in sequential order based on steps of use and orders of multiple medical examination devices, in order to instruct the user on how to use those medical examination devices through a speaker;
superimposing symbols of the real-time mimesis graphic, in order to instruct the user on how to use the medical examination devices;
expressing behavior of the user or executing mimesis thereof in real time while monitoring use conditions of the medical examination devices by the camera;
demanding correction of errors while monitoring use conditions of the medical examination devices by the camera and expressing behavior of the user or executing mimesis thereof in real time;

superimposing different symbols of the real-time mimesis graphic on position information of the presently used medical examination device and standard medical examination position information, in order to provide specific information to the user in real time, wherein the user can recognize a degree of leaving the standard medical examination position from the specific information;

storing the measured data metered by the medical examination device or transmitting the same to a remote medical diagnosis server; and conducting self-analysis of the metered data from the medical examination device by medical examination software and notifying the user of diagnosis results wherein the suction holes are equidistantly spaced apart from one another, and the length of the respective suction holes gradually increases toward one end of the vacuum suction device.

28. The diagnostic method according to claim 20, further comprising:

recognizing the body of a user via a camera and transmitting the recognized images in real time to the remote doctor or demonstrating the same on a monitor screen;

generating voice commands in sequential order based on steps of use and orders of multiple medical examination devices by the remote doctor, in order to instruct the user on how to use those medical examination devices through a speaker;

superimposing instruction cursors provided by the remote doctor on the monitor screen, in order to instruct the user on how to use the medical examination devices;

demanding correction of errors while monitoring use conditions of the medical examination devices by the camera;

storing the measured data metered by the medical examination device or transmitting the same to a remote medical diagnosis server and the remote doctor; and conducting analysis of the metered data from the medical examination device by the remote doctor and notifying the user of diagnosis results through a message transfer tool.

29. The diagnostic method according to claim 20, further comprising:

recording use conditions of the medical examination device used by the user, by recognizing the same using a camera, recording and storing the recognized results;

transmitting the measurement data metered by the medical examination device and results of recording the use conditions to the remote doctor as well as a remote medical diagnosis server; and analyzing the metered data and the recorded results of the use conditions by the remote doctor and notifying the user of diagnosis results via a message transfer tool.

* * * * *